United States Patent
Rozzell et al.

(10) Patent No.: US 6,835,212 B2
(45) Date of Patent: Dec. 28, 2004

(54) AGENT AND METHOD FOR DYEING KERATIN FIBERS

(75) Inventors: David Rozzell, Burbank, CA (US); Guido Sauter, Marly (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 168 days.

(21) Appl. No.: 10/181,572

(22) PCT Filed: Oct. 5, 2001

(86) PCT No.: PCT/EP01/11493

§ 371 (c)(1), (2), (4) Date: Jul. 18, 2002

(87) PCT Pub. No.: WO02/47633

PCT Pub. Date: Jun. 20, 2002

(65) Prior Publication Data

US 2003/0041391 A1 Mar. 6, 2003

(30) Foreign Application Priority Data

Dec. 13, 2000 (DE) .......................... 100 62 086

(51) Int. Cl.⁷ ................................. A61K 7/13
(52) U.S. Cl. .............. 8/405; 8/409; 8/410; 8/412; 8/574; 8/602; 8/611; 548/480; 548/461
(58) Field of Search ............... 8/405, 409, 410, 8/412, 574, 602, 611; 548/460, 461

(56) References Cited

U.S. PATENT DOCUMENTS

| | | | |
|---|---|---|---|
| 3,251,742 A | 5/1966 | Saul ............................ 167/88 |
| 5,605,793 A | 2/1997 | Stemmer ....................... 435/6 |
| 5,830,721 A | 11/1998 | Stemmer et al. .......... 435/172.1 |
| 5,837,458 A | 11/1998 | Minshull et al. ............... 435/6 |
| 5,881,238 A | 3/1999 | Aman et al. ........... 395/200.56 |
| 5,958,672 A | 9/1999 | Short ............................. 435/4 |
| 5,965,408 A | 10/1999 | Short ........................ 435/91.1 |
| 6,001,574 A | 12/1999 | Short et al. .................... 435/6 |
| 6,152,967 A | 11/2000 | Maubru ......................... 8/401 |
| 6,306,181 B1 * | 10/2001 | Terranova et al. ............. 8/409 |
| 2002/0059682 A1 | 5/2002 | Hoeffkens et al. ............. 8/405 |

FOREIGN PATENT DOCUMENTS

| | | |
|---|---|---|
| DE | 197 17 281 A1 | 10/1998 |
| DE | 299 08 646 U1 | 9/1999 |
| DE | 199 49 033 A1 | 4/2001 |
| DE | 100 45 856 A1 | 3/2002 |
| EP | 0 107 834 | 5/1984 |
| GB | 1 320 250 A | 6/1973 |
| WO | 01 47478 A | 7/2001 |

OTHER PUBLICATIONS

G.L. Lemiere: "Alcohol Dehydronase Catalysed Oxidoreduction Reactions . . .", M. P. Schneider (ED), Enzymes as Catalysts in Organic Synthesis, 1986, pp. 19–34.

J. Bryan Jones and Etsuo Takemura: "Enzymes in Organic Synthesis . . . ", Can. J. Chem. 62, 1984, pp. 77–80.

Ze'ev Shaked et al: "Enzyme–Catalyzed Organic Synthesis . . . " J. Am. Chem. Soc. 102, 1980, pp. 7104–7105.

Preparative Biotransformations (S.M. Roberts, Editor), Chapter 3, pp. 3.1.1.–3.1.6., John Wiley & Sons, Chichester, UK, 1997.

* cited by examiner

Primary Examiner—Margaret Einsmann
Assistant Examiner—Eisa Elhilo
(74) Attorney, Agent, or Firm—Michael J. Striker

(57) ABSTRACT

The agent for dyeing keratin fibers contains one or more aryl and/or benzyl alcohols, one or more oxidizing enzymes, especially vanillyl oxidase, derivatives of vanillyl oxidase or galactose oxidase, and a nucleophilic compound that forms a dye for dyeing keratin fibers in the presence of the alcohols and enzymes. A method for dyeing keratin fibers with this agent is also disclosed. Two-component kits for performing the method of dyeing keratin fibers include a first compenent (A) and a second component (B) separate from the first component. The first component (A) includes the nucleophilic compound, the alcohol and optionally the oxidizing enzyme. The second component (B) includes the oxidizing enzyme when it is not included in the first component or more alcohol.

9 Claims, No Drawings

AGENT AND METHOD FOR DYEING KERATIN FIBERS

The present invention relates to an agent and to a method for dyeing keratin fibers, especially human hair.

The reaction between ketones or aldehydes, especially aromatic aldehydes such as benzaldehyde and various substituted benzaldehydes, with compounds having an active CH group, water being split off and compounds formed, which are suitable for dyeing keratin fibers, has already been described earlier, for example, in the German Offenlegungsschrift 197 17 281 and the German utility patent 299 08 464. The possibility of sensitizing when the ketone or the aldehyde is applied directly on the hair or the scalp is a disadvantage of using this reaction between ketones or aldehydes and compounds with active CH groups. Furthermore, it is difficult to incorporate especially aldehydes into the dyeing agents and to keep such agents for longer periods, since the aldehydes tend to oxidize in air, forming carboxylic acids, which do not participate in the color-forming reaction.

The present application avoids the direct use of ketones or aldehydes by employing primary or secondary alcohols as aldehyde or ketone precursors for the aforementioned reaction, the alcohols being oxidized enzymatically in situ to the corresponding aldehydes or ketones.

The object of the present application therefore is an agent for dyeing keratin fibers, especially wool, silk or hair, especially human hair, wherein at least one compound with a nucleophilic reaction center, at least one alcohol from the group comprising aryl alcohol derivatives and benzyl alcohol derivatives and at least one oxidizing enzyme is contained.

As inventive alcohol, especially aryl alcohols or benzyl alcohols of formula (I) may be named, which can be converted by enzyme-catalyzed oxidation to the corresponding carbonyl compounds;

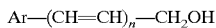

in which n=0, 1 or 2;
and Ar is a group of formula

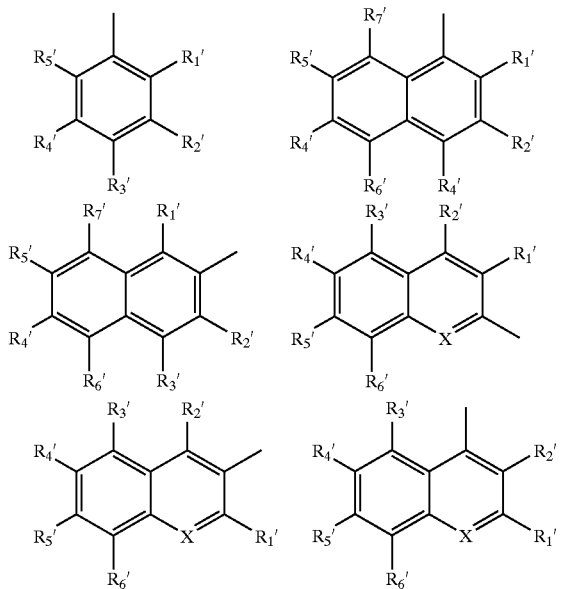

in which Y is an oxygen atom, a sulfur atom or an $NR^a$ group; R1', R2', R3', R4', R5', R6' and R7' independently of one another are a hydrogen atom, a hydroxy group, a methoxy group, an aryl group, a halogen atom (F, Cl, Br, I), a —CHO— group, a —$COR^a$ group, a —$CO_2R^a$ group, an $NO_2$— group, an —$OCOR^a$ group, an —$OCH_2$aryl group, an —$NH_2$ group, an —$NH_3^+$ group, an —$NHR^a$ group, an —$NH_2R^{a+}$ group, an —$N(R^a)_2$ group, an —$N(R^a)_3^+$ group, an —$NHCOR^a$ group, an —$NHCOOR^a$ group, in which $R^a$ is a hydrogen atom, a linear or branched C1 to C4 alkyl group, an optionally substituted, aromatic, carbocyclic group or heterocyclic group, or R4' and R5' together with the carbon atom of the aromatic ring form a 5-membered or 6-membered alicyclic or aromatic ring, which optionally may contain one or more sulfur, nitrogen or oxygen atoms.

The following compounds of formula (I) are particularly preferred: benzyl alcohol, 4-hydroxy-benzyl alcohol, 4-hydroxy-3-methoxy-benzyl alcohol (vanillyl alcohol), 3-hydroxy-4-methoxy-benzyl alcohol (isovanillyl alcohol), 3,5-dimethoxy-4-hydroxybenzyl alcohol, 3,4-dihydroxy-benzyl alcohol, 2-hydroxy-3-methoxy-benzyl alcohol, 4-ethoxy-benzyl alcohol, 4-carboxy-benzyl alcohol, 2,5-dihydroxy-benzyl alcohol, 2,4-dihydroxy-benzyl alcohol, 2-hydroxy-benzyl alcohol, 3,5-dimethoxy-4-hydroxy-benzyl alcohol, 4-hydroxy-2-methoxy-benzyl alcohol, 2,4-dimethoxy-benzyl alcohol, 2,3-dimethoxy-benzyl alcohol, 2,5-dimethoxy-benzyl alcohol, 3,5-dimethoxy-benzyl alcohol, 3,4-methylenedioxy-benzyl alcohol, 3,4- dimethoxy-benzyl alcohol, 3-ethoxy-4-hydroxy-benzyl alcohol, 3,5-dimethyl-4-hydroxy-benzyl alcohol, 3,4-dimethoxy-5-hydroxy-benzyl alcohol, 3,4,5-trimethoxy-benzyl alcohol, 2,4,6-trihydroxy-benzyl alcohol, 3,4,5-trihydroxy-benzyl alcohol, 2,3,4-trihydroxy-benzyl alcohol, 3,5-di-t-butyl-4-hydroxy-benzyl alcohol, 2-nitro-benzyl alcohol, 3-nitro-benzyl alcohol, 4-nitro-benzyl alcohol, 2-amino-benzyl alcohol, 3-amino-benzyl alcohol, 3-amino-4-methyl-benzyl alcohol, 3,5-diamino-benzyl alcohol, 4-amino-benzyl alcohol, 4-dimethylamino-benzyl alcohol, 4-diethylamino-2-hydroxy-benzyl alcohol, 4-diethylamino-3-methoxy-benzyl alcohol, 4-dimethylamino-2-methoxy-benzyl alcohol, 4-dibutyl-amino-benzyl alcohol, 3-methoxy-4-(1-pyrrolidinyl)-benzyl alcohol, (4-methoxy-naphthalene-1-yl)-methanol, (4-dimethylamino-naphthalene-1-yl)-methanol, 2-(hydroxymethyl)-1-naphthol, 1-naphthalene-methanol, 2-naphthalene-methanol, (2-methoxy-naphthalene-1-yl)-methanol, 4-hydroxy-methyl-naphthalene-1-ol, 4'-hydroxymethyl-biphenyl-4-ol, (4-hydroxymethylphenyl)-methanol, 4-(3-hydroxy-propenyl)-2-methoxy-phenol, 4-(3-hydroxy-propenyl)-2,6-dimethoxy-phenol, 3-(4-dimethylaminophenyl)-prop-2-ene-1-ol, 5-(4-(diethylamino-phenyl)-penta-2,4-diene-1-ol, thiophene-2-yl-methanol, (5-hydroxymethyl-thiophene-2-yl)-methanol, thiophene-3-yl-methanol, (1H-pyrrole-2-yl)-methanol, (1-methyl-1H-pyrrole-2-yl)-methanol, (5-methyl-furan-2-yl)-methanol, (1H-indole-3-yl)-methanol, and (6-methyl-1H-indole-3-yl)-methanol.

The use of the alcohol instead of the corresponding carbonyl compound of the present invention makes a rapid intensive dyeing of the fibers, especially of the keratin fibers possible in the presence of a compound with a nucleophilic center with the addition of an oxidizing enzyme. "An oxidizing enzyme" is understood here to be an enzyme, which is able to catalyze the oxidation of the alcohol to an aldehyde or ketone. The following are named as examples of such enzymes, which are, however, not limited to these: alcohol dehydrogenases (E.C. Classification 1.1.1.-), alcohol oxidases (E.C. Classification 1.1.2- and 1.1.3- and 1.1.99-), flavinoxidases (E.C. Classification 1.2.--), laccases (E.C. Classification 1.4.---), peroxidases (E.C. Classification 1.11.1.-), hydroxylases and monooxygenases (E.C. Classification 1.13.12- and 1.13.99-).

The enzyme is used preferably in an amount of 5 to 100 units per millimole of substrate (alcohol). A unit of enzyme activity refers here to the amount of enzyme, which is required to catalyze the oxidation of 1 micromole of alcohol per minute.

"Compounds with a nucleophilic reaction center" are understood to be compounds, which are able to form unsaturated carbon-carbon or carbon-nitrogen bonds by reaction with the electrophilic carbonyl carbon of the aldehyde or ketone. Suitable compounds with a nucleophilic reaction center of the present invention are, for example, primary or secondary aliphatic or aromatic amines, nitrogen-containing heterocyclic compounds, amino acids, oligopeptides with 2 to 9 amino acid groups, aromatic hydroxy compounds and compounds with active CH group.

Suitable compounds with primary or secondary amino groups are, for example, primary aromatic amines such as N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-dichloro-p-phenylenediamine, 2,4-dichloro-p-phenylenediamine, 2,5-dichloro-p-phenylenediamine, 2-chloro-p-phenylenediamine, 2,5-dihydroxy-4-morpholinoaniline dihydrobromide, 2-aminophenol, 3-aminophenol, 4-aminophenol, 2-aminomethyl-4-aminophenol, 2-hydroxymethyl-4-aminophenol, o-phenylenediamine, m-phenylenediamine, p-phenylenediamine, o-toluylenediamine, m-toluylenediamine, 2,5-diaminotoluene, 2,5-diaminophenol, 2,5-diaminophenethol, 4-amino-3-methylphenol, 2,4-diaminophenoxyethanol, 2-(2,5-diamino-phenyl)-ethanol, 2-(2,5-diaminophenoxy)-ethanol, 4-methylaminoaniline, 3-amino-(2-hydroxyethyloxy) aniline, 3,4-methylenediaminoaniline, 3,4-methylenedioxyaniline, 3-amino-2,4-dichloro-phenol, 4-methylamino-phenol, 2-methyl-5-amino-phenol, 3-methyl-4-amino-phenol, 2-methyl-5-(2-hydroxyethylamino)-phenol, 6-methyl-3-amino-2-chloro-phenol, 2-methyl-5-amino-4-chloro-phenol, 5-(2-hydroxyethylamino)-4-methoxy-2-methyl-phenol, 1,3-diamino-2,4-dimethoxybenzene, 2-aminobenzoic acid, 3-aminobenzoic acid, 4-aminobenzoic acid, 2,3-diaminobenzoic acid, 2,4-diaminobenzoic acid, 2,4-diaminobenzoic acid, 2,5-diaminobenzoic acid, 3,4-diaminobenzoic acid, 3,5-diaminobenzoic acid, 4-aminosalicylic acid, 5-amino-salicylic acid, 3-amino-4-hydroxy-benzoic acid, 4-amino-3-hydroxy-benzoic acid, 2-aminobenzenesulfonic acid, 3-aminobenzenesulfonic acid, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaminobenzene, 2,4,6-triaminoresorcinol, 4,5-diaminopyrocatechol, 4,6-diaminopyrogallol, 3,5-diamino-4-hydroxypyrocatechol, aromatic anilines or phenols with a further aromatic group, such as 4,4'-diaminostilbene, 4,4'-diaminostilbene-2,2'-disulfonic acid monosodium salt or 4,4'-diaminostilbene-2,2'-disulfonic acid disodium salt, 4,4-diamino-diphenylmethane, 4,4-diaminodiphenylsulfide, 4,4-diaminodiphenylsulfoxide, 4,4-diaminodiphenylamine, 4,4-diaminodiphenylamine-2-sulfonic acid, 4,4'-diaminiobenzophenone, 4,4'-diamininobenzophenone diphenyl ether, 3,3',4,4'-tetraaminodiphenyl), 3,3',4,4'-tetraamino-benzophenone, 1,3-bis-(2,4-diaminophenoxy)-propane, 1,8-bis-(2,5-diaminophenoxy)-3,6-dioxaoctane, 1,3-bis-(4-aminophenylamino)-propane, 1,3-bis-(4-aminophenylamino)-2-propanol, 1,3-bis-[N-(4-aminophenyl)-2-hydroxyethyl-amino]-2-propanol, N,N-bis-[2,(4-aminophenoxy)-ethyl]-methylamine and N-phenyl-1,4-phenylenediamine.

Suitable nitrogen-containing heterocyclic compounds are, for example, 2-aminopyridine, 3-aminopyridine, 4-aminopyridine, 2-amino-3-hydroxy-pyridine, 2,6-diaminopyridine, 2,5-diaminopyridine, 2,3-diaminopyridine, 2-dimethylamino-5-aminopyridine, 2-methylamino-3-amino-6-methoxy-pyridine, 2,3-diamino-6-methoxypyridine, 2,6-dimethoxy-3,5-diaminopyridine, 2,4,5-triaminopyridine, 2,6-dihydroxy-3,4-dimethylpyridine, 2,4-dihydroxy-5,6-diamino-pyrimidine, 4,5-triamino-pyrimidine, 4-hydroxy-2,5,6-triamino-pyrimidine, 2-hydroxy-4,5,6-triamino-pyrimidine, 2,4,5,6-tetraamino-pyrimidine, 2-methylamino-4,5,6-triamino-pyrimidine, 2,4-diamino-pyrimidine, 4,5-diaminopyrimidine, 2-amino-4-methoxy-6-methyl-pyrimidine, 3,5-diaminopyrazole, 3,5-diamino-1,2,4-triazole, 3-aminopyrazole, 3-amino-5-hydroxypyrazole, 2-aminoquinoline, 3-aminoquinoline, 8-aminoquinoline, 4-aminoquinaldine, 2-aminonicotinic acid, 6-aminonicotinic acid, 5-amino-isoquinoline, 5-aminoindazole, 6-aminoindazole, 5-aminobenzimidazole, 7-aminobenzimidazole, 7-amino-benzothiazole, 5-amino-benzothiazole, 2,5-dihydroxy-4-morpholinoaniline as well as indole and indolin derivatives, such as 4-aminoindole, 5-aminoindole, 6-aminoindole, 7-aminoindole, 5,6-dihydroxyindole, 5,6-dihydroxyindoline and 4-hydroxyindoline.

The aforementioned amines and heterocyclic compounds can be used in free form as well as in the form of the physiologically tolerated salts, such as salts of inorganic acids like hydrochloric acid or sulfuric acid.

All naturally occurring and synthetic amino acids, such as arginine, histidine, tyrosine, phenylalalanine, dihydroxyphenylalanine, ornithine, lysine and tryptophane come into consideration as amino acids.

As oligopeptides, all naturally occurring or synthetic oligopeptides, as well as the oligopeptides contained in polypeptide or protein hydrolysates, can be used, provided that they are sufficiently soluble for use in the inventive dyeing agents. Glutathione or the oligopeptides, contained in the hydrolysates of collagen, keratin, casein, elastin, soybean protein, wheat gluten or almond protein, are named as examples. In this connection, the joint use of the oligopeptides with compounds with a primary or a secondary amino group or with aromatic hydroxy compounds is preferred.

Suitable aromatic hydroxy compounds are, for example, 2-methylresorcinol, 4-methylresorcinol, 5-methylresorcinol, 2,5-dimethylresorcinol, resorcinol, 3-methoxyphenol, pyrocatechol, hydroquinone, pyrogallol, phloroglucinol, hydroxyhydroquinone, 2-methoxyphenol, 3-methoxyphenol, 4-methoxyphenol, 3-dimethylaminophenol, 2-(2-hydroxyethyl)-phenol, 3,4-methylenedioxyphenol, 2,4-dihydroxybenzoic acid, 3,4-dihydroxy-benzoic acid, 2,4-dihydroxy-phenylacetic acid, 3,4-dihydroxyphenylacetic acid, gallic acid, 2,4,6-trihydroxybenzoic acid, 2,4,6-trihydroxy-acetophenone, 2-chlororesorcinol, 4-chlororesorcinol, 1-naphthol, 1,5-dihydroxynaphthalene, 2,3-dihydroxy-naphthalene, 2,7-dihydroxynaphthalene, 4-hydroxy-2-naphthalene sulfonic acid and 3,6-dihydroxy-2,7-naphthalene sulfonic acid.

As suitable compounds with an active CH group, 1,2,3,5-tetramethyl-3H-indolium iodide, 1,2,3,5-tetramethyl-3H-indolium methosulfate, 2,3-dimethyl-benzothiazolium iodide, 2,3-dimethyl-benzothiazolium-p-toluenesulfonate, rhodanine, rhodanine-3-acetic acid, 1-ethyl-2-quinaldinium iodide, 1-methyl-2-quinaldinium iodide, barbituric acid, thiobarbituric acid, 1,3-dimethyl-thiobarbituric acid, 1,3-diethyl-thiobarbituric acid, oxindole, 3-indoxyl acetate, cumaranone, 1-methyl-3-phenyl-2-pyrazolinone and enamines of Formula (II) or their salts of Formula (IIa),

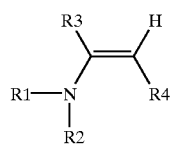

(II)

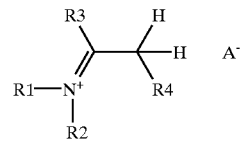

(IIa)

in which R1 is a single ring or multi-ring aromatic group, especially a 5-membered or 6-membered aryl group (preferably a phenyl group), which optionally is substituted by a C1 to C4 alkyl group, a C1 to C4 hydroxyalkyl group, a hydroxy group, a methoxy group, a dialkylamino group or a halogen group (F, Ck, Br, I), a 5-membered or 6-membered hetero cyclic ring (preferably a pyridyl group or a naphthyl group), which optionally is substituted by a C1 to C4 alkyl group, a C1 to C4 hydroxyalkyl group, a hydroxy group, a methoxy group, a dialkylamino group or a halogen group (F, Cl, Br, I); R2 is a linear or branched C1 to C8 alkyl group, a linear or branched C1 to C8 hydroxyalkyl group or a C1 to C8 alkoyalkyl group, possibly with oxygen atoms between the carbon atoms of the alkyl chain; R3 is a linear or branched C1 to C8 alkyl group, a C1 to C8 alkoxyalkyl group, a linear or branched C1 to C8 alkylene group, a C1 to C8 alkoxy alkylene group, an oxygen atom, a sulfur atom, an —NH group or an —NR group, in which R is an alkyl group, an alkoxyalkyl group, a hydroxyalkyl group or hydrogen, a cyclic compound possibly being formed by the R1 and R3 groups together with the nitrogen atom and the carbon atom of the basic enamine structure, and R4 is hydrogen, a linear C1 to C4 alkyl group or a branched C1 to C4 alkyl group and A⁻ is the anion of an organic or inorganic acid.

Especially preferred compounds with a nucleophilic reaction center are the following enamines of Formulas (III) to (X), in which X is a carbon atom with two C1 to C4 alkyl groups, which may be the same or different (especially 2 methyl groups), a carbon atom, substituted by a C1 to C4 alkyl group, and a carbon atom, substituted by a hydroxy group, a sulfur atom, an alkylated nitrogen atom, a not alkylated nitrogen atom or an oxygen atom; and R2 is a linear or branched C1 to C8 alkyl group, a linear or branched C1 to C8 hydroxyalkyl group or a C1 to C8 alkoxyalkyl group, oxygen atoms possibly being present between the carbon atoms of the alkyl chain; R4 is hydrogen, a linear C1 to C4 alkyl group or a branched C1 to C4 group; R5, R6, R7 and R8 independently of one another are hydrogen, a linear or branched C1 to C4 alkyl group, a linear or branched C1 to C4 hydroxyalkyl group, a hydroxy group, a methoxy group, an amino group, a mono(C1 to C4) alkylamino group, a di(C1 to C4) alkylamino group, a benzyl group or a halogen atom (F, Cl, Br, I); and A⁻ is chloride, bromide, iodide, sulfate, hydrogen sulfate, toluenesulfonate, benzenesulfonate, monomethyl sulfate, hexafluorophosphate, hexafluoroantimonate, tetrafluoroborate, tetraphenylborate, formate, acetate or propionate, the chloride ion, tetrafluoroborate ion, the acetate ion and the hydrogen sulfate ion being particularly preferred.

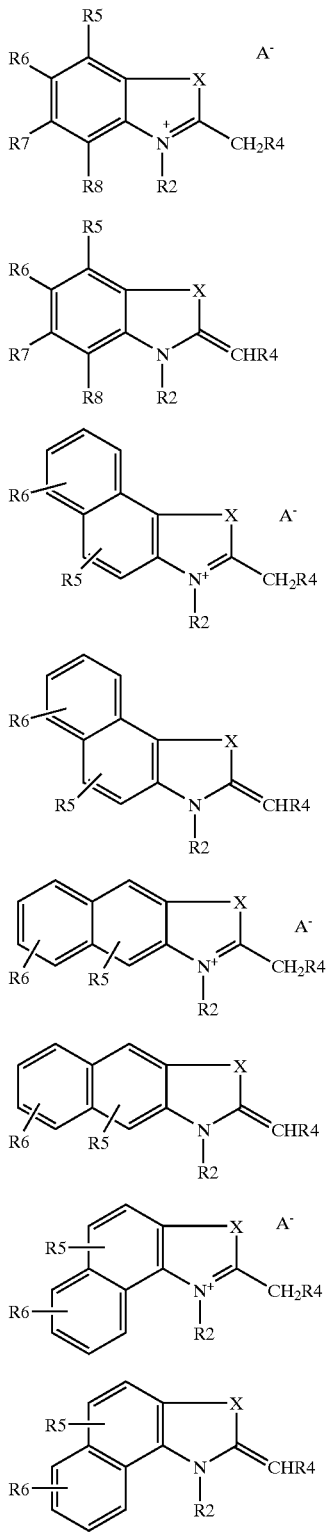

The following compounds with nucleophilic reaction centers are preferred: 1,3,3-trimethyl-2-methylene-indoline as well as its salts,
1,3,3,4-tetramethyl-2-methylene-indoline as well as its salts,
1,3,3,5-tetramethyl-2-methylene-indoline as well as its salts,
1,3,3,6-tetramethyl-2-methylene-indoline as well as its salts,
1,3,3,7-tetramethyl-2-methylene-indoline as well as its salts,
1,3,3,6,7-pentamethyl-2-methylene-indoline as well as its salts,
1,3,3,5,7-pentamethyl-2-methylene-indoline as well as its salts,
1,3,3,4,7-pentamethyl-2-methylene-indoline as well as its salts,
5-chloro-1,3,3-trimethyl-2-methylene-indoline as well as its salts,
5-fluoro-1,3,3-trimethyl-2-methylene-indoline as well as its salts,
5-isopropyl-1,3,3-trimethyl-2-methylene-indoline as well as its salts,
5-hydroxy-1,3,3-trimethyl-2-methylene-indoline as well as its salts,
5-methoxy-1,3,3-trimethyl-2-methylene-indoline as well as its salts,
5-amino-1,3,3-trimethyl-2-methylene-indoline as well as its salts,
5-nitro-1,3,3-trimethyl-2-methylene-indoline as well as its salts,
5-N-acetylamino-1,3,3-trimethyl-2-methylene-indoline as well as its salts,
6-hydroxy-1,3,3-trimethyl-2-methylene-indoline as well as its salts,
6-methoxy-1,3,3-trimethyl-2-methylene-indoline as well as its salts,
5-methoxy-6-nitro-1,3,3-trimethyl-2-methylene-indoline as well as its salts,
5-methoxy-6-N-acetylamino-1,3,3-trimethyl-2-methylene-indoline as well as its salts,
5-methoxy-6-amino-1,3,3-trimethyl-2-methylene-indoline as well as its salts,
5,6-methylenedioxy-1,3,3-trimethyl-2-methylene-indoline as well as its salts,
5,6-dihydroxy-1,3,3-trimethyl-2-methylene-indoline as well as its salts,
5,6-dimethoxy-1,3,3-trimethyl-2-methylene-indoline as well as its salts,
4,5-dihydroxy-1,3,3-trimethyl-2-methylene-indoline as well as its salts,
5,7-dihydroxy-1,3,3-trimethyl-2-methylene-indoline as well as its salts,
5-amino-6-methoxy-1,3,3-trimethyl-2-methylene-indoline as well as its salts,
5-amino-7-hydroxy-1,3,3-trimethyl-2-methylene-indoline as well as its salts,
5-hydroxy-7-amino-1,3,3-trimethyl-2-methylene-indoline as well as its salts,
5-hydroxy-7-N-acetylamino-1,3,3-trimethyl-2-methylene-indoline as well as its salts,
1-methyl-3-spiro-cyclopropyl-2-methylene-indoline as well as its salts,
1-methyl-3-spiro-cyclohexyl-2-methylene-indoline as well as its salts,
1-methyl-3-spiro-cyclohexyl-5-hydroxy-2-methylene-indoline as well as its salts,
1-methyl-3-spirocyclohexyl-5-methoxy-2-methylene-indoline as well as its salts,
1-(2'-hydroxyethyl)-3,3-dimethyl-2-methylene-indoline as well as its salts,
1,3,3-trimethyl-2-methylene-3H-benz[e]indole as well as its salts and N-ethyl-2-methylene-benzthiazole as well as its salts; the 5-nitro-1,3,3-trimethyl-2-methylene-indoline, 5-methoxy-6-nitro-1,2,3,3-tetramethyl-3H-indolium-chloride, 5-N-acetylamino-1,2,3,3-tetramethyl-3H-indolium acetate, 1,3,3-trimethyl-2-methylene-indoline, 1,2,3,3-tetramethyl-3H-indolium chloride, 1,2,3,3-tetramethyl-3H- indolium bromide, 1,2,3,3-tetramethyl-3H-indolium iodide, 1,2,3,3-tetramethyl-3H-indolium sulfate, 1,2,3,3-tetramethyl-3H-indolium-hydrogen sulfate, 1,2,3,3-tetramethyl-3H-indolium methyl sulfate, 1,2,3,3-tetramethyl-3H-indolium hexafluorophosphate, 1,2,3,3-tetramethyl-3H-indolium hexafluoro antimonate, 1,2,3,3-tetramethyl-3H-indolium tetrafluoroborate, 1,2,3,3,5-pentamethyl-3H-indolium iodide, 1,2,3,3,7-pentamethyl-3H-indolium tetrafluoroborate, 1,2,3,3,6,7-hexamethyl-3H-indolium tetrafluoroborate, 1,2,3,3,5,7-hexamethyl-3H-indolium tetrafluoroborate, 1,2,3,3,4,7-hexamethyl-3H-indolium tetrafluoroborate, 5-chloro-1,2,3,3-tetramethyl-3H-indolium iodide, 5-fluoro-1,2,3,3-tetramethyl-3H-indolium iodide, 5-isopropyl-1,2,3,3-tetramethyl-3H-indolium iodide, 5-methoxy-1,2,3,3-tetramethyl-3H-indolium iodide, 5-hydroxy-1,2,3,3-tetramethyl-3H-indolium iodide, 1,2,3,3-tetramethyl-3H-benz[e]indolium chloride, 1,2,3,3-tetramethyl-3H-benz[e]indolium bromide, 1,2,3,3-tetramethyl-3H-benz[e]indolium iodide, 1,2,3,3-tetramethyl-3H-benz[e]indolium sulfate, 1,2,3,3-tetramethyl-3H-benz[e]indolium hexafluorophosphate, 1,2,3,3-tetramethyl-3H-benz[e]indolium methyl sulfate, 1,2,3,3-tetramethyl-3H-benz[e]indolium hexafluoro antimonate, 1,2,3,3-tetramethyl-3H-benz[e]indolium tetrafluoroborate, 1,2-dimethyl-benzthiazolium iodide, 5-methoxy-6-N-acetylamino-1,2,3,3-tetramethyl-3H-indolium acetate, 5-hydroxy-6-N-acetylamino-1,2,3,3-tetramethyl-3H-indolium acetate and N-ethyl-2-methylbenzthiazolium iodide being especially preferred.

The alcohol and the compound with a nucleophilic reaction center are used in each case in a total amount of about 0.05 to 25% by weight and preferably of 0.2 to 15% by weight, based on the ready-for-use agent.

As already mentioned above, alcohol dehydrogenases, alcohol oxidases, various flavin oxidases, laccases, peroxidases or similar enzymes can be used as oxidizing enzymes pursuant to the present invention. In a preferred embodiment of the invention, alcohol dehydrogenase as oxidizing enzyme, the oxidation being carried out in the presence of a suitable co-factor, such as the nicotinamide co-factor.

As "nicotinamide co-factor" NAD+, NADP+ and a variety of derivatives, which affect the enzymatic oxidation of alcohol to aldehyde advantageously, can be used, for example. Such co-factors and their derivatives are known to those skilled in the art. These co-factors can be used in an amount approximately equimolar to the amount of alcohol or, if desired, the co-factor can be recovered. A plurality of methods for recovering the co-factor has become known from the art and any of these known methods can be used in the present invention. Suitable methods for recovering the co-factor are described, for example, in G. L. Lemiere, J. A. Lepoivre, and F. C. Aldenweireldt, Tetrahedron Letters, 26, 4257 (1985); in "Enzymes as Catalysts for Organic Synthesis," pp. 19–34, M. Schneider, Ed., Reidel Dordecht, 1986; Z. Shaked and G. M. Whitesides, J. Am. Chem. Soc. 102, 7104–5 (1980); J. B. Jones and T. Takamura, Can. J. Chem. 62, 77 (1984). In Preparative Biotransformations (S. M. Roberts, editor), Chapter 3, pages 3.1.1–3.1.6, John Wiley & Sons, Chichester, U.K. (1997), a recovery method is described, for which flavin mononeucleotides (FMN) are used, which transfer electrons to the oxygen, which functions as the ultimate oxidizing agent. For this method, 0.0005 to 0.05 moles of NAD+ or NADP+ are used per mole of diol, which is to be oxidized. This represents a recovery factor for a co-factor of about 20 to 2000.

In a further preferred embodiment of the present invention, flavin oxidase, which catalyses the oxidation of alcohol to aldehyde using molecular oxygen as oxidant, is used as oxidizing enzyme. The use of galactose oxidase as oxidizing enzyme is particularly preferred. Likewise, the use of vanillyl alcohol oxidase as oxidizing enzyme is particularly preferred. The use of derivative of the galactose oxidase or of the vanillyl alcohol oxidase is also particularly preferred. A "derivative" is understood here to be an enzyme variant, which is obtained by a mutagenesis of the original enzyme by means of known methods. Examples of such mutagenesis are selective evolution, DNA shuffling, molecular breeding, gene rearrangement and recombination, random mutation, point mutation, gene site saturation mutagenesis, etc. Such methods are also known from the art, for example, from U.S. Pat. Nos. 5,605,793, 5,811,238, 5,830,721, 5,837,458, 5,965,408, 5,958,672 and 6,001,574. Gene encoding derivatives, if desired, can be planned and/or produced by inserting preferred codons.

Furthermore, compounds from the group of direct dyes, such as aromatic nitro dyes, azo dyes, anthraquinone dyes or triphenylmethane dyes, can be added alone or in admixture with one another to optimize the dyeing result and to produce special color effects.

Examples of nitro dyes are picramic acid, 4-(2',3'-dihydroxypropyl)-amino-3-nitro-trifluoro-methylbenzene, 4,N-ethyl-N-(2'-hydroxyethyl)-amino-1-(2'-hydroxyethyl)-amino-2-nitrobenzene, 2-chloro-6-ethylamino-4-nitrophenol, 1-hydroxy-2-β-hydroxy-ethylamino-4,6-dinitrobenzene, 4-(2'-hydroxyethyl)-amino-3-nitrochlorobenzene, 2-amino-6-chloro-4-nitrophenol and 4-(2'-hydroxyethyl)amino-3-nitro-methylbenzene.

Examples of azo dyes are 1-(2'-methoxyphenylazo)-2-hydroxy-7-trimethyl-ammonium-naphthalene (Basic Red 76), 4-(4'-sulfo-1-phenylazo)-1-(4"-sulfophenyl)-3-carboxy-5-hydroxypyrazolone (Acid Yellow 23), 4-amino-4'-bis[2"-hydroxyethyl]-amino-azobenzene (Disperse Black 9) and 1-(4'-aminophenylazo)-2-hydroxy-7-trimethyl-ammonium naphthalene (Basic Brown 16).

Examples of anthraquinone dyes are 1-methylamino-4-(2'-hydroxyethyl)amino-anthraquinone (Disperse Blue 3), 1-amino-4-hydroxy-anthraquinone (Disperse Red 15), 2-methoxy-1,4-diamino-anthraquinone (Disperse Red 11), 1,4-diamino-anthraquinone (Disperse Violet 1), 1-amino-4-methylamino-anthraquinone (Disperse Violet 4), 1,4-bis(2', 3'-dihydroxypropyl)amino-anthraquinone, 1-methylamino-4-(amino-n-propyltrimethyl-ammonium)-anthraquinone (Basic Blue 22), 1,4-bis-(2-hydroxyethyl)amino-5,8-dihydroxy-anthraquinone (Disperse Blue 7) and 1-methylamino-4-aminopropylamino-anthraquinone (HC Blue 8).

Examples of triphenylmethane dyes are [4-[[4-diethylamino]phenyl]-[4-(ethylamino)-1-naphthalinyl]methylene]-2,5-cyclohexadiene-1-ylidene]-N-ethyl-ethanamine (Basic Blue 7) and 4',4',4"-triamino-3-methyltriphenyl-carbenium chloride (Basic Violet 14, Fuchsin AN).

The amount of direct dyes added preferably is 0.01% to 5% by weight and especially 0.1% to 4% by weight.

The inventive agent represents a mixture of the components with the additives, which are customary for such preparation.

Conventional, cosmetic additives, are, for example, solvents such as water, low molecular weight, aliphatic, monohydric or multihydric alcohols, their esters and ethers, such as alkanols, especially with 1 to 4 carbon atoms in the alkyl chain, such as ethanol, n-propanol or i-propanol, butanol, i-butanol, dihydric or trihydric alcohols, especially those with 2 to 6 carbon atoms, such as ethylene glycol, propylene glycol, 1,3-dihydroxypropane, 1,4-dihydroxybutane 1,5-dihydroxypentane, 1,6-dihydroxyhexane, 1,2,6-trihydroxyhexane, glycerin, diethylene glycol, dipropylene glycol, polyalkylene glycols, such as triethylene glycol, polyethylene glycol, tripropylene glycol and polypropylene glycol, lower molecular weight alkyl ethers of multihydric-alcohols, such as ethylene glycol monomethyl ether, ethylene glycol monoethyl ether, ethylene glycol monopropyl ether, ethylene glycol monobutyl ether, diethylene glycol monomethyl ether or diethylene glycol monoethyl ether, triethylene glycol monomethyl ether, triethylene glycol monoethyl ether, ketones and ketoalcohols, especially those with 3 to 7 carbon atoms in the molecule, such as acetone, methyl ethyl ketone, diethyl ketone, methyl isobutyl ketone, methyl phenyl ketone, cyclopentanone, cyclohexanone and diacetone alcohol, ethers, such as dibutyl ether, tetrahydrofuran, dioxane or diisopropyl ether esters, such as ethyl formate, methyl formate, methyl acetate, ethyl acetate, propyl acetate, butyl acetate, phenyl acetate, ethylene glycol monoethyl ether acetate or hydroxyethyl acetate, amides, such as dimethylformamide, dimethylacetamide or N-methyl-pyrrolidone; as well as urea, tetramethylurea and thiodiglycol, furthermore wetting agents or emulsifiers from the classes of anionic, cationic, amphoteric, nonionic or zwitterionic, surface active substances, such as fatty alcohol sulfates, alkylsulfonates, alkylbenzenesulfonates, alkyltrimethylammonium salts, alkylbetaines, $\alpha$-olefinsulfonates, ethoxylated fatty alcohols, ethoxylated nonylphenols, fatty acid alkanolamines, ethoxylated fatty acid ester, fatty alcohol polyglycol ether sulfates, alkyl polyglucosides, thickening agents, such as higher molecular weight fatty alcohols, starch, cellulose derivatives, Vaseline, paraffin oil, fatty acids and other fat components in emulsified form, water-soluble, polymeric thickening agents, such as natural gums, guar gum, xanthan gum, carob seed flour, pectin, dextran, agar-agar, amyloses, amylopectin, dextrins, clays or fully synthetic hydrocolloids, such as polyvinyl alcohol, moreover, cosmetics such as lanolin derivatives, cholesterol, pantothenic acid, water soluble cationic polymers, protein derivatives, pro-vitamins, vitamins, plant extracts, sugar and betaine, auxiliary materials, such as electrolytes, antioxidants, fatty amides, sequestering agents, film-forming agents, and preservatives.

The constituents mentioned are used in amounts customary for such purposes. For example, the wetting agents and emulsifiers are used in concentrations of about 0.5 to 30% by weight, the thickeners in an amount of 0.1 to 25% by weight and the cosmetics in a concentration of about 0.1 to 5.0% by weight.

Normally, the individual constituents of the inventive dyeing agents must be stored separately from one another and are mixed together immediately before use. The inventive agents can be produced in various ways. For example, the agents may be in the form of a 2-component kit, which consists of a component (A) containing the compound with a nucleophilic reaction center, the alcohol, optionally the nicotinamide co-factor and/or the buffer, and a component (B), containing the oxidizing enzyme as well as optionally the nicotinamide co-factor and/or the buffer. In a further, preferred, embodiment, the 2-component kit consists of a component (A), containing the compound with a nucleophilic reaction center, the alcohol and the oxidizing enzyme, as well as, optionally, the nicotinamide co-factor and/or the buffer, and a component (B), containing the alcohol, as well as, optionally, the nicotinamide co-factor and/or the buffer. Preferably, components (A) and/or (B) are anhydrous, that is, they contain not more than 1% by weight of water, and are mixed with water, which may contain additional, conventional cosmetic additives, only before use.

The constituents of the inventive dyeing agent, that is, the alcohol, the compound with a nucleophilic carbon and the oxidizing enzyme, as well as, optionally, the nicotinamide co-factor and/or the buffer, can also be packed together, provided that they are anhydrous, that is, provided that they do not contain more than 1% by weight of water, and are mixed with water, which may contain additional conventional cosmetic additives, only before use.

It is also possible to package the co-factor and the buffer separately and to mix them before use with the remaining components of the agent (3- or 4-component kit).

The dyeing of keratin fibers is usually carried out in an aqueous medium. Mixtures, which contain at least 60% by weight of water and more preferably at least about 70% by weight of water are regarded as "aqueous media".

The pH of the ready-for-use dyeing agent is about 2 to 12, preferably about 4 to 10 and particularly about 6 to 9.

The individual components are mixed together before use and the ready-for-use agent, so obtained, is then applied on the keratin fibers, which are to be dyed, water or an aqueous preparation, containing the usual cosmetic additives, optionally being added. The mixture is left on the fibers, for example, on hair, for about 10 to 45 minutes and preferably for about 30 to 40 minutes at about 10° to 70° C. and preferably at about 15° to 50° C., after which the fibers are rinsed with water and dried.

Dyeings with outstanding fastness properties, especially with respect to light fastness, wash fasteners and rubbing fastness, especially on hair, are made possible by the inventive dyeing agents and dyeing method.

The object of the invention is described in greater detail by the following examples, without being limited to these

EXAMPLES

Examples 1 to 8

Use of Galactose Oxidase for Dyeing Hair in the Presence of 1,2,3,3-tetramethyl-3H-indolium Hydrogen Sulfate and Substituted Benzyl Alcohols Galactose oxidase, as a lyophilized powder, the appropriately substituted benzyl alcohol of Table 1, as well as 1,2,3,3-tetramethyl-3H-indolium hydrogen sulfate are mixed together in a 50 mL centrifuge tube, the mixture of the aforementioned components being diluted with water to a total volume of about 30 mL.

The hair was treated for 40 minutes at 37° C. with the dyeing solutions of Table 1. Enzyme (galactose oxidase) was present in Examples 1 to 4 and absent in Examples 5 to 8 (=control group). Subsequently the hair was washed with water and dried. The dyeing results are summarized in Table 2.

TABLE 1

| Example No. | Alcohol (250 mmoles/L stock solution in DMSO) | Galactose oxidase | 1,2,3,3-tetramethyl-3H-indolium hydrogensulfate | Potassium phosphate buffer (250 mmoles/L stock solution) | $H_2O$ |
|---|---|---|---|---|---|
| 1 | Vanillyl alcohol: 1.2 mL (final concentration: 10 mmoles/L) | 30 mg (200 units) | 80 mg (final concentration: 10 mmoles/L) | 6 mL (final concentration: 100 mmoles/L) | 22.8 mL |
| 2 | Isovanillyl alcohol: 1.2 mL (final concentration: 10 mmoles/L) | 30 mg (200 units) | 80 mg (final concentration: 10 mmoles/L) | 6 mL (final concentration: 100 mmoles/L) | 22.8 mL |
| 3 | p-hydroxy-benzyl alcohol: 1.2 mL (final concentration 10 mmoles/L) | 30 mg (200 units) | 80 mg (final concentration: 10 mmoles/L) | 6 mL (final concentration: 100 mmoles/L) | 22.8 mL |
| 4 | p-amino-benzyl alcohol: 1.2 mL (final concentration: 10 mmoles/L) | 30 mg (200 units) | 80 mg (final concentration: 10 mmoles/L) | 6 mL (final concentration: 100 mmoles/L) | 22.8 mL |
| 5 | Vanillyl alcohol: 1.2 mL (final concentration: 10 mmoles/L) | — | 80 mg (final concentration: 10 mmoles/L) | 6 mL (final concentration: 100 mmoles/L) | 22.8 mL |
| 6 | Isovanillyl alcohol: 1.2 mL (final concentration: 10 mmoles/L) | — | 80 mg (final concentration: 10 mmoles/L) | 6 mL (final concentration: 100 mmoles/L) | 22.8 mL |
| 7 | p-hydroxy-benzyl alcohol: 1.2 mL (final concentration: 10 mmoles/L) | — | 80 mg (final concentration: 10 mmoles/L) | 6 mL (final concentration: 100 mmoles/L) | 22.8 mL |
| 8 | p-amino-benzyl alcohol: 1.2 mL (final concentration: 10 mmoles/L) | — | 80 mg (final concentration: 10 mmoles/L) | 6 mL (final concentration: 100 mmoles/L) | 22.8 mL |

TABLE 2

| Example No. | Color Result |
|---|---|
| 1 | red |
| 2 | yellow-orange |
| 3 | orange |
| 4 | intense pink |
| 5 | weak pink |
| 6 | weak pink |
| 7 | weak pink |
| 8 | weak pink |

Examples 1 to 4 resulted in intensive colors. On the other hand, comparison Examples 5 to 8, which did not contain any galactose oxidase, resulted only in a weak coloration Example 9

The Use of Horse Liver Alcohol Dehydrogenase for the in Situ Oxidation of Substituted Benzyl Alcohols in the Presence of 1,2,3,3-tetramethyl-3H-indolium Hydrogen Sulfate.

The horse liver alcohol dehydrogenase-catalyzed oxidation of benzyl alcohol in the presence of 1,2,3,3-tetramethyl-3H-indolium hydrogen sulfate was carried out in a potassium phosphate buffer system (100 mmoles per liter; pH=7) as follows. Solutions containing 2 to 15 mmoles per liter of 1,2,3,3-tetramethyl-3H-indolium hydrogen sulfate were prepared. Subsequently, equimolar amounts of 2 mmoles/L solutions, containing the appropriate benzyl alcohol, were added and the total volume was made up to 1 mL with buffer solution. Thereupon, 0.25 mm of oxidized nicotinamide co-factor (NAD+), as well as 10 units of horse liver alcohol dehydrogenase were added. The color development reaction was observed at room temperature as a function of reaction time. After a period of observation of not more than 1 hour, the colors summarized in the Table 3 below resulted:

TABLE 3

| Benzyl Alcohol Derivate | Color |
|---|---|
| Benzyl alcohol | pink |
| Vanillyl alcohol | red |
| Isovanillyl alcohol | yellow-orange |
| p-Hydroxybenzyl alcohol | orange |

Example 10

Color Intensities as a Function of the Concentration of 1,2,3,3-tetramethyl-3H-indolium hydrogen sulfates and of the substituted benzyl alcohol The color reaction was carried out, as in Example 9, at room temperature in a potassium phosphate system with horse liver alcohol dehydrogenase (10 units/mL), NAD+, 1,2,3,3,-tetramethyl-3H-indolium hydrogen sulfate and substituted benzyl alcohol being used in equimolar amounts, which varied from 2 to 10 mmoles/L. The color intensity obtained was proportional to the concentration used, a concentration of 10 mmoles/L giving more intensive colorations than a concentration of 2 mmoles/L.

Example 11

Hair Dyeing

Dyeing solutions were prepared as in Examples 1 to 4. However, instead of the galactose oxidase, 400 units of horse liver alcohol dehydrogenase, from which the ammonium ions had been removed by dialysis, were used. Subsequently, the hair was dyed as described in Examples 1 to 4.

The color results are summarized in the following Table.

TABLE 4

| Benzyl Alcohol Derivative | Color |
|---|---|
| Vanillyl alcohol | red |
| Isovanillyl alcohol | yellow |
| p-Hydroxybenzyl alcohol | orange |
| p-Aminobenzyl alcohol | pink |

In the present application, all enzyme concentrations are reported in "units" of the international measured variable, which is recommended by the International Union For Biochemistry as the standard for all types of enzymes.

Unless stated otherwise, all percentages are percentages by weight.

What is claimed is:

1. An agent for dyeing keratin fibers, said agent containing at least one compound with a nucleophilic reaction center, at least one aryl alcohol and at least one oxidizing enzyme;

wherein said at least one compound with said nucleophilic reaction center reacts with said at least one aryl alcohol and said at least one oxidizing enzyme to form a dye for the keratin fibers;

wherein the at least one compound with the nucleophilic reaction center is selected from the group consisting of 1,3,3-trimethyl-2-methylene-indoline,
1,3,3,4-tetramethyl-2-methylene-indoline,
1,3,3,5-tetramethyl-2-methylene-indoline,
1,3,3,6-tetramethyl-2-methylene-indoline,
1,3,3,7-tetramethyl-2-methylene-indoline,
1,3,3,6,7-pentamethyl-2-methylene-indoline,
1,3,3,5,7-pentamethyl-2-methylene-indoline,
1,3,3,4,7-pentamethyl-2-methylene-indoline,
5-chloro-1,3,3-trimethyl-2-methylene-indoline,
5-fluoro-1,3,3-trimethyl-2-methylene-indoline,
5-isopropyl-1,3,3-trimethyl-2-methylene-indoline,
5-hydroxy-1,3,3-trimethyl-2-methylene-indoline,
5-methoxy- 1,3,3-trimethyl-2-methylene-indoline,
5-amino- 1,3,3- trimethyl-2-methylene-indoline,
5-nitro-1,3,3-trimethyl-2-methylene-indoline,
5-N-acetylamino-1,3,3-trimethyl-2-methylene-indoline,
6-hydroxy- 1,3,3-trimethyl-2-methylene-indoline,
6-methoxy-1,3,3-trimethyl-2-methylene-indoline,
5-methoxy-6-nitro-1,3,3-trimethyl-2-methylene-indoline,
5-methoxy-6-N-acetylamino-1,3,3-trimethyl-2-methylene-indoline,
5-methoxy-6-amino-1,3,3-trimethyl-2-methylene-indoline,
5,6-methylenedloxy-1,3,3-trimethyl-2-methylene-indoline,
5,6-dihydroxy-1,3,3-trimethyl-2-methylene-indoline,
5,6-dimethoxy-1,3,3-trimethyl-2-methylene-indoline,
4,5-dihydroxy-1,3,3-trimethyl-2-methylene-indoline,
5,7-dihydroxy-1,3,3-trimethyl-2-methylene-indoline,
5-amino-6-methoxy-1,3,3-trimethyl-2-methylene-indoline,
5-amino-7-hydroxy-1,3,3-trimethyl-2-methylene-indoline,
5-hydroxy-7-amino-1,3,3-trimethyl-2-methylene-indoline,
5-hydroxy-7-N-acetylamino-1,3,3-trimethyl-2-methylene-indoline.
1-methyl-3-spiro-cyclopropyl-2-methylene-indoline,
1-methyl-3-spiro-cyclohexyl-2-methylene-indoline,
1-methyl-3spiro-cyclohexyl-5-hydroxy-2-methylene-indoline,
1methyl-3spirocyclohexyl-5-hydroxy-2-methylene-indoline,
1-(2'-hydroxyethyl)-3,3-dimethyl-2-methylene-indoline,
1,3,3-trimethyl-2-methylene-3H-benzindole and
N-ethyl-2-methylene-benzthiazole; or a salt thereof.

2. The agent as defined in claim 1, wherein said at least one aryl alcohol is selected from the group consisting of benzyl alcohol, 4-hydroxy-benzyl alcohol, 4-hydroxy-3-methoxybenzyl alcohol, 3-hydroxy-4-methoxy-benzyl alcohol, 3,5-dimethoxy-4hydroxybenzyl alcohol, 3,4-dihydroxybenzyl alcohol, 2-hydroxy-3-methoxybenzyl alcohol, 4-ethoxybenzyl alcohol, 4-carboxy-benzyl alcohol, 2,5-dihydroxybenzyl alcohol, 2,4-dihydroxy-benzyl alcohol, 2-hydroxybenzyl alcohol, 3,5-dimethoxy-4-hydroxybenzyl alcohol, 4-hydroxy-2-methoxybenzyl alcohol, 2,4-dimethoxybenzyl alcohol, 2,3-dimethoxybenzyl alcohol, 2,5-dimethoxybenzyl alcohol, 3,5-dimethoxybenzyl alcohol, 3,4-methylene-dioxybenzyl alcohol, 3,4-dimethoxybenzyl alcohol, 3-ethoxy-4-hydroxybenzyl alcohol, 3,5-dimethyl-4-hydroxybenzyl alcohol, 3,4-dimethoxy-5-hydroxybenzyl alcohol, 3,4,5-trimethoxybenzyl alcohol, 2,4,6-trihydroxybenzyl alcohol, 3,4,5-trihydroxybenzyl alcohol, 2,3,4-tri-hydroxybenzyl alcohol, 3,5-di-t-butyl-4-hydroxybenzyl alcohol, 2-nitrobenzyl alcohol, 3-nitrobenzyl alcohol, 4-nitrobenzyl alcohol, 2-aminobenzyl alcohol, 3-aminobenzyl alcohol, 3-amino-4-methylbenzyl alcohol, 3,5-diaminobenzyl alcohol, 4-aminobenzyl alcohol, 4-dimethylamino-benzyl alcohol, 4-diethylamino-2-hydroxybenzyl alcohol, 4-diethylamino-3-methoxybenzyl alcohol, 4-dimethylamino-2-methoxybenzyl alcohol, 4-dibutylaminobenzyl alcohol, 3-methoxy-4-(1-pyrrolidinyl)-benzyl alcohol, (4-methoxy-naphthalene-1-yl)-methanol, (4-dimethylamino-naphthalene-1-yl)-methanol, 2-(hydroxymethyl)-1-naphthol, 1-naphthalene-methanol, 2-naphthalene-methanol, (2-methoxy-naphthalene-1-yl)-methanol, 4-hydroxy-methyl-naphthalene-1-ol, 4'-hydroxy-methyl-biphenyl-4-ol, (4-hydroxymethyl-phenyl)-methanol, 4-(3-hydroxy-propenyl)-2-methoxyphenol, 4-(3-hydroxy-propenyl)-2,6,-dimethoxyphenol, 3-(4-dimethylaminophenyl)-prop-2-ene-1-ol, 5-(4-(diethylaminophenyl)-penta-2,4-diene-1-ol, thiophene-2-yl-methanol, (5-hydroxymethylthiophene-2-yl)-methanol, thiophene-3-yl-methanol, (1H-pyrrole-2-yl)-methanol, (1-methyl-1H-pyrrole-2-yl)-methanol, (5-methylfuran-2-yl)-methanol, (1H-indole-3-yl)-methanol, and (6-methyl-1H-indole-3-yl)-methanol.

3. The agent as defined in claim 1, wherein, the at least one oxidizing enzyme is selected from the group consisting of alcohol dehydrogenases, alcohol oxidases, flavin oxidases, laccases, peroxidases, hydroxylases and monooxygenases.

4. The agent as defined in claim 1, wherein said at least one oxidizing enzyme is selected from the group consisting of vanillyl oxidase, derivatives of vanillyl oxidase and derivatives of galactose oxidase.

5. An agent for dyeing keratin fibers in the form of a 2-component kit, comprising a component (A) and a component (B) separate from said component (A);
wherein said component (A) contains a compound with a nucleophilic reaction center, an aryl alcohol and optionally a nicotinamide co-factor and a butter, and said component (B) contains an oxidizing enzyme and optionally the nicotinamide co-factor and the buffer; and
wherein said compound with said nucleophilic reaction center reacts with said alcohol and said oxidizing enzyme to form a dye for the keratin fibers; and
wherein said compound with said nucleophilic reaction center is selected from the group consisting of
1,3,3-trimethyl-2-methylene-indoline,
1,3,3,4-tetramethyl-2-methylene-indoline,
1,3,3,5-tetramethyl-2-methylene-indoline,
1,3,3,6-tetramethyl-2-methylene-indoline,
1,3,3,7-tetramethyl-2-methylene-indoline,
1,3,3,6,7-pentamethyl-2-methylene-indoline,
1,3,5,7-pentamethyl-2-methylene-indoline,
1,3,3,4,7-pentamethyl-2-methylene-indoline,
5-chloro-1,3,3-trimethyl-2-methylene-indoline,
5-fluoro-1,3,3-trimethyl-2-methylene-indoline,
5-isopropyl-1,3,3-trimethyl-2-methylene-indoline,
5-hydroxy-1,3,3-trimethyl-2-methylene-indoline,
5-methoxy-1,3,3-trimethyl-2-methylene-indoline,
5-amino-1,3,3-trimethyl-2-methylene-indoline.
5-nitro-1,3,3trimethyl-2-methylene-indoline.
5-N-acetylamino-1,3,3-trimethyl-2-methylene-indoline,
6-hydroxy-1,3,3-trimethyl-2-methylene-indoline,
6-methoxy-1,3,3-trimethyl-2-methylene-indoline,
5methoxy-6-nitro-1,3,3-trimethyl-2-methylene-indoline,
5-methoxy-6-N-acetylamino-1,3,3-trimethyl-2-methylene-indoline,
5-methoxy-6-amino-1,3,3-trimethyl-2-methylene-indoline,
5,6-methylenedioxy-1,3,3-trimethyl-2-methylene-indoline,
5,6-dihydroxy-1,3,3-trimethyl-2-methylene-indoline,
5,6-dimethoxy-1,3,3-trimethyl-2-methylene-indoline,
4,5-dihydroxy-1,3,3-trimethyl-2-methylene-indoline,
5,7-dihydroxy-1,3,3-trimethyl-2-methylene-indoline,
5-amino-6-methoxy-1,3,3-trimethyl-2-methylene-indoline,
5-amino-7-hydroxy-1,3,3-trimethyl-2-methylene-indoline,
5-hydroxy-7-amino-1,3,3-trimethyl-2-methylene-indoline,
5-hydroxy-7-N-acetylamino-1,3,3-trimethyl-2-methylene-indoline,
1-methyl-3-spiro-cyclopropyl-2-methylene-indoline,
1-methyl-3-spiro-cyclohexyl-2-methylene-indoline,
1-methyl-3-spiro-cyclohexyl-5-hydroxy-2-methylene-indoline,
1-methyl-3-spirocyclohexyl-5-methoxy-2-methylene-indoline,
1-(2'-hydroxyethyl)-3,3-dimethyl-2-methylene-indoline,
1,3,3-trimethyl-2-methylene-3H-benzindole and
N-ethyl-2-methylene-benzthiazole; or a salt thereof.

6. An agent for dyeing keratin fibers in the form of a 2-component kit, comprising a component (A) and a component (B) separate from said component (A);
wherein said component (A) contains a compound with a nucleophilic reaction center, an aryl alcohol, an oxidizing enzyme and optionally a nicotinamide co-factor and a buffer, and said component (B) contains said alcohol and optionally the nicotinamide co-factor and the buffer; and
wherein said compound with said nucleophilic reaction center reacts with said alcohol and said oxidizing enzyme to form a dye for the keratin fibers; and
wherein said compound with said nucleophilic reaction center is selected from the group consisting of
1,3,3-trimethyl-2-methylene-indoline,
1,3,3,4-tetramethyl-2-methylene-indoline,
1,3,3,5-tetramethyl -2-methylene-indoline,
1,3,3,6-tetramethyl-2-methylene-indoline,
1,3,3,7-tetramethyl-2-methylene-indoline,
1,3,3,6,7-pentamethyl-2-methylene-indoline,
1,3,3,5,7-pentamethyl-2-methylene-indoline,
1,3,3,4,7-pentamethyl-2-methylene-indoline,
5-chloro-1,3,3-trimethyl-2-methylene-indoline,
5-fluoro-1,3,3-trimethyl-2-methylene-indoline,
5-isopropyl-1,3,3-trimethyl-2methylene-indoline,
5-hydroxy-1,3,3-trimethyl-2-methylene-indoline,
5-methoxy-1,3,3-trimethyl-2-methylene-indoline,
5-amino-1,3,3- trimethyl-2-methylene-indoline,
5-nitro-1,3,3-trimethyl-2-methylene-indoline,
5-N-acetylamino-1,3,3-trimethyl-2-methylene-indoline,
6-hydroxy-1,3,3-trimethyl-2-methylene-indoline,
6-methoxy-1,3,3-trimethyl-2-methylene-indoline,
5-methoxy-6-nitro-1,3,3-trimethyl-2-methylene-indoline,
5-methoxy-6-N-acetylamino-1,3,3-trimethyl-2-methylene-indoline,
5-methoxy-6-amino-1,3,3-trimethyl-2-methylene-indoline,
5-methylenedloxy-1,3,3-trimethyl-2-methylene-indoline,
5,6-dihydroxy-1,3,3-trimethyl-2-methylene-indoline,
5,6-dimethoxy-1,3,3-trimethyl-2-methylene-indoline,
4,5-dihydroxy-1,3,3-trimethyl-2-methylene-indoline,
5,7-dihydroxy-1,3,3-trimethyl-2-methylene-indoline,
5-amino-6-methoxy-1,3,3-trimethyl-2-methylene-indoline,
5-amino-7-hydroxy-1,3,3-trimethyl-2-methylene-indoline,
5-hydroxy-7-amino-1,3,3-trimethyl-2-methylene-indoline,
5-hydroxy-7-N-acetylamino-1,3,3-trimethyl-2-methylene-indoline,
1-methyl-3-spiro-cyclopropyl-2-methylene-indoline,
1-methyl-3-spiro-cyclohexyl-2-methylene-indoline,
1-methyl-3-spiro-cyclohexyl-5-hydroxy-2-methylene-indoline,
1-methyl-3-spirocyclohexyl-5-methoxy-2-methylene-indoline,
1-(2'-hydroxyethyl)-3,3-dimethyl-2-methylene-indoline,
1,3,3-trimethyl-2-methylene-3H-benzindole and
N-ethyl-2-methylene-benzthiazole; or a salt thereof.

7. The agent as defined in claim 1, consisting of an anhydrous agent and prior to dyeing the keratin fibers said anhydrous agent is mixed with water or an aqueous preparation containing cosmetic additive ingredients.

8. A method of dyeing keratin fibers, said method comprising the steps of:
  a) providing an agent for dyeing keratin fibers containing at least one compound with a nucleophilic reaction center, at least one aryl alcohol and at least one oxidizing enzyme, wherein said at least one compound with said nucleophilic reaction center reacts with said at least one aryl alcohol and said at least one oxidizing enzyme to form a dye for the keratin fibers;
  b) applying said agent to keratin fibers to be dyed; and
  c) after the applying of step b), allowing said agent to act on said keratin fibers for from 10 to 45 minutes at a temperature of 15° C. to 50° C.; and
  d) after the allowing of step c), rinsing said keratin fibers and subsequently drying; and
  wherein said at least one compound with said nucleophilic reaction center is selected from the group consisting of 1,3,3-trimethyl-2-methylene-indoline,
  1,3,3,4-tetramethyl-2-methylene-indoline,
  1,3,3,5-tetramethyl-2-methylene-indoline,
  1,3,3,6-tetramethyl-2-methylene-indoline,
  1,3,3,7-tetramethyl-2-methylene-indoline,
  1,3,3,6,7-pentamethyl-2-methylene-indoline,
  1,3,3,5,7-pentamethyl-2-methylene-indoline,
  1,3,3,4,7-pentamethyl-2-methylene-indoline,
  5-chloro-1,3,3-trimethyl-2-methylene-indoline,
  5-fluoro-1,3,3-trimethyl-2-methylene-indoline,
  5-isopropyl-1,3,3-trimethyl-2-methylene-indoline,
  5-hydroxy-1,3,3-trimethyl-2-methylene-indoline,
  5-methoxy-1,3,3-trimethyl2-methylene-indoline,
  5-amino-1,3,3-trimethyl-2-methylene-indoline,
  5-nitro-1,3,3-trimethyl-2-methylene-indoline,
  5-N-acetylamino-1,3,3-trimethyl-2-methylene-indoline,
  6-hydroxy-1,3,3-trimethyl-2-methylene-indoline,
  6-methoxy-1,3,3-trimethyl-2-methylene-indoline,
  5-methoxy-6-nitro-1,3,3-trimethyl-2-methylene-indoline,
  5-methoxy-6-N-acetylamino-1,3,3-trimethyl-2-methylene-indoline,
  5-methoxy-6-amino-1,3,3-trimethyl-2-methylene-indoline,
  5,6-methylenedloxy-1,3,3-trimethyl-2-methylene-indoline,
  5,6-dihydroxy-1,3,3-trimethyl-2-methylene-indoline,
  5,6-dimethoxy-1,3,3-trimethyl-2-methylene-indoline,
  4,5-dihydroxy-1,3,3-trimethyl-2-methylene-indoline,
  5,7-dihydroxy-1,3,3-trimethyl-2-methylene-indoline,
  5-amino-6-methoxy-1,3,3-trimethyl-2-methylene-indoline,
  5-amino-7-hydroxy-1,3,3-trimethyl-2-methylene-indoline.
  5-hydroxy-7-amino-1,3,3-trimethyl-2-methylene-indoline,
  5-hydroxy-7-N-acetylamino-1,3,3-trimethyl-2-methylene-indoline,
  1-methyl-3-spiro-cyclopropyl-2-methylene-indoline,
  1-methyl-3-spiro-cyclohexyl-2-methylene-indoline,
  1-methyl-3-spiro-cyclohexyl-5-hydroxy-2-methylene-indoline,
  1-methyl-3-spirocyclohexyl-5-methoxy-2-methylene-indoline,
  1-(2'-hydroxyethyl)-3,3-dimethyl-2-methylene-indoline,
  1,3,3-trimethyl-2-methylene-3H-benzindole and
  N-ethyl-2-methylene-benzthiazole; or a salt thereof.

9. The agent as defined in claim 1, wherein said aryl alcohols are each of formula (I):

Ar—(CH=CH)$_n$—CH$_2$OH            (I), wherein n=0, 1 or 2 and Ar is a group having one of the following formulae:

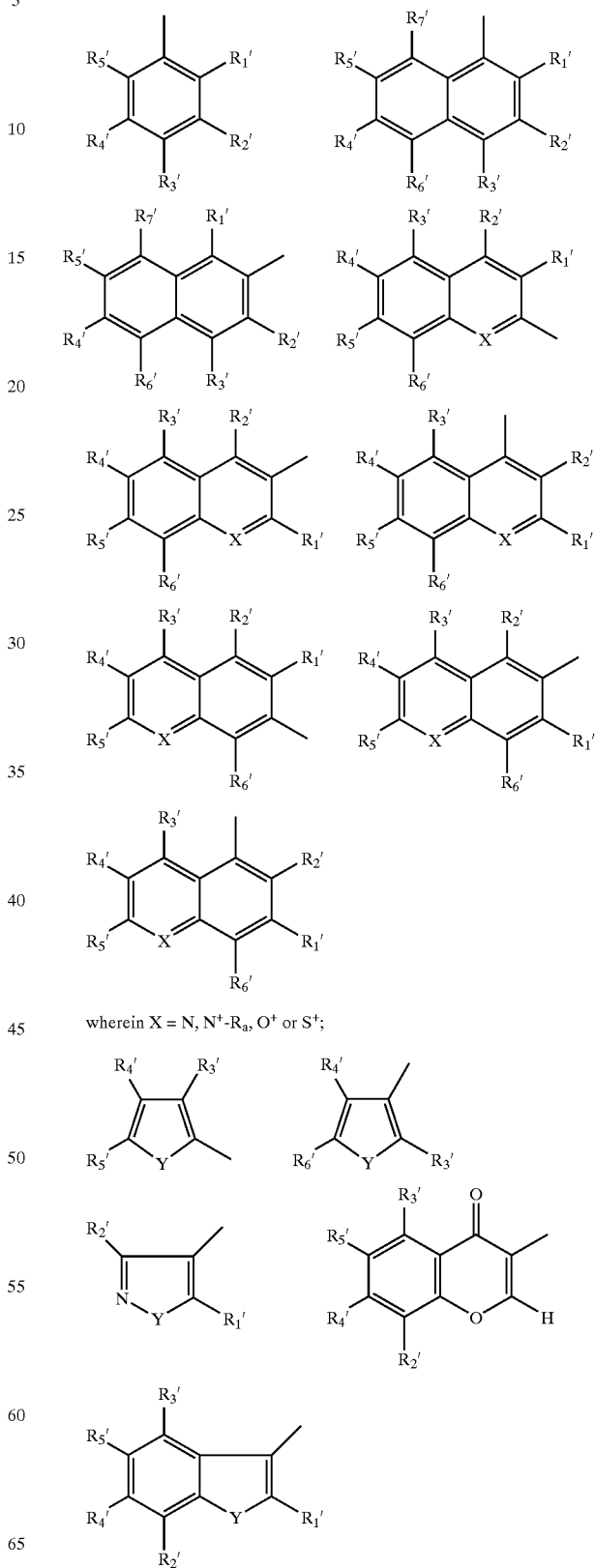

wherein X = N, N$^+$-R$_a$, O$^+$ or S$^+$;

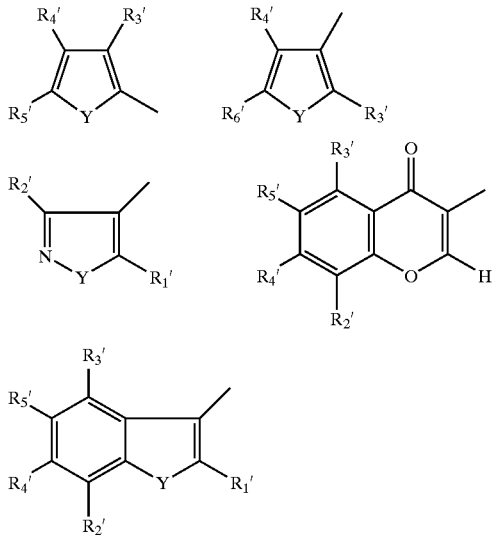

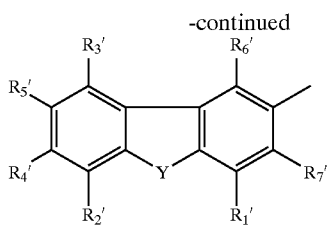

wherein Y is an oxygen atom, a sulfur atom or a $NR^a$ group; R1', R2', R3', R4', R5', R6' and R7', independently of one another, are each a hydrogen atom, a hydroxy group, a methoxy group, an aryl group, a halogen atom, a —CHO group, a —$COR^a$ group, a —$CO_2R^a$ group, an $NO_2$-group, an —$OCOR^a$ group, an —$OCH_2$-aryl group, an —$NH_2$ group, an —$NH_3^{30}$ group, an —$NHR^a$ group, an —$NH_2R^a$ group, an —$N(R^a)_2$ group, an —$N(R^a)_3^+$ group, an —$NHCOR^a$ group, an —$NHCOOR^a$ group, in which $R^a$ is a hydrogen atom, a linear or branched C1 to C4 alkyl group, an optionally substituted, aromatic, carbocyclic group or heterocyclic group, or R4' and R5' together with a carbon atom of an aromatic ring of said Ar form a 5-member or 6-member alicyclic or aromatic ring, which optionally may contain one or more sulfur, nitrogen or oxygen atoms.

* * * * *